United States Patent [19]
L'Esperance, Jr.

[11] Patent Number: 4,931,053
[45] Date of Patent: Jun. 5, 1990

[54] METHOD AND APPARATUS FOR ENHANCED VASCULAR OR OTHER GROWTH

[75] Inventor: Francis A. L'Esperance, Jr., Englewood, N.J.

[73] Assignee: L'Esperance Medical Technologies, Inc., New York, N.Y.

[21] Appl. No.: 148,980

[22] Filed: Jan. 27, 1988

[51] Int. Cl.$^5$ .............................................. A61N 5/00
[52] U.S. Cl. ........................................ 606/2; 606/4; 606/10; 128/395
[58] Field of Search .................... 128/303.1, 395, 392, 128/398; 606/2–4, 9, 10, 13, 17, 18

[56] References Cited

U.S. PATENT DOCUMENTS

| | | | |
|---|---|---|---|
| 3,096,767 | 7/1963 | Gresser et al. | 128/303.1 |
| 3,914,013 | 10/1975 | Rosenberg | 128/303.1 |
| 4,266,549 | 5/1981 | Kimura | 128/303.1 |
| 4,289,378 | 9/1981 | Remy et al. | 128/303.1 |
| 4,315,130 | 2/1982 | Inagaki et al. | 219/121.6 |
| 4,336,809 | 6/1982 | Clark | 128/398 |
| 4,391,275 | 7/1983 | Fankhauser | 128/303.1 |
| 4,454,882 | 6/1984 | Takano | 128/395 |
| 4,561,436 | 12/1985 | Munnerlyn | 128/303.1 |
| 4,705,036 | 11/1987 | Hughes et al. | 128/303.1 |

FOREIGN PATENT DOCUMENTS

| | | | |
|---|---|---|---|
| 253734 | 1/1988 | European Pat. Off. | 128/303.1 |
| 2577425 | 8/1986 | France | 128/395 |
| 511079 | 8/1976 | U.S.S.R. | 128/303.1 |
| 1143429 | 3/1985 | U.S.S.R. | 128/303.1 |
| 1113928 | 5/1985 | U.S.S.R. | 128/395 |
| 1073914 | 6/1985 | U.S.S.R. | 128/303.1 |
| 1258422 | 9/1986 | U.S.S.R. | 128/303.1 |
| 2108282 | 5/1983 | United Kingdom | 128/303.1 |

OTHER PUBLICATIONS

"Fiber Bundle Scanner . . . " by Fujii et al., Optics & Laser Tech., vol. 14, No. 1, 2/82, pp. 39–40.
"A Method for Estimating Aortic Atheromatosis" by Edholm et al., The Lancet, 3/7/64, pp. 535–536.

Primary Examiner—Max Hindenburg
Assistant Examiner—David Shay
Attorney, Agent, or Firm—Hopgood, Calimafde, Kalil, Blaustein & Judlowe

[57] ABSTRACT

The invention comtemplates promotion or enhanced promotion of vascular or other growth in living body tissue through effectively concurrent in-vivo delivery of at least two beams of laser irradiation at an affected area of body tissue, wherein the irradiation (a) is of low intensity at tissue impingement and (b) is also of spectral wavelength that is preferably in the visible red or in the infrared. Perturbations result in affected cells either directly by reason of differences in the physical properties of the respective beams or indirectly by reason of interaction between the two beams at or near the situs of delivery to the affected body tissue.

44 Claims, 2 Drawing Sheets

METHOD AND APPARATUS FOR ENHANCED VASCULAR OR OTHER GROWTH

BACKGROUND OF THE INVENTION

The invention relates to the use of laser radiation to promote or enhance vascular or other growth in a thus-irradiated local area of living body tissue.

In their paper, "Some New Findings on Retinal Irradiation by Krypton and Argon Lasers",* J. Marshall, et al. review the histopathology of the acute effects of krypton and argon laser radiation on the human retina, and these effects are related to their long-term pathology by observations on diabetics. Emphasis was on laser photocoagulation but some "surprising findings" were reported involving proliferation of vascular endothelial cells adjacent the reaction site. And in a later paper, "He-Ne Laser Stimulation of Human Fibroblast Proliferation and Attachment in Vitro",** coauthored by J. Marshall, laboratory studies are reported for laser-irradiated cultures of excised human tissues, wherein the irradiation source was a 1 mW helium-neon laser providing a coherent source at 633 nm, wherein the irradiation was chopped at 100 Hz, to provide a 50 percent duty cycle; for each experiment, a comparative run was made involving monochromatic incoherent light via a 640-nm interference filter (bandwidth 9 nm), adjusted for intensity comparable with that of laser delivery to an identical culture. The reported result was that, at 24 and at 48 hours after 15-minute exposure, the particular laser-irradiated cultures exhibited a significant increase in the number of cells in comparison with their respective non-irradiated controls, while no significant change in cell counts was observed between irradiated and control cultures in experiments with the incoherent source.

* *Docum. Ophthal. Proc. Series,* Vol. 36, pp. 21-37, 1984, Dr. W. Junk Publishers, The Hague.
** *Lasers in the Life Sciences* 1(2), 1986, pp. 125-134, Harwood Academic Publishers GmbH.

BRIEF STATEMENT OF THE INVENTION

It is an object of the invention to provide an improved method and means for in-vivo laser irradiation of living-body tissue.

It is a specific object to achieve the above object using perturbation effects induced by multiple beams of laser irradiation delivered to affected body tissue.

Another specific object is to achieve the above objects without inducing photocoagulation, photooptical-tissue breakdown, photovaporization, or photoablative decomposition of the affected body tissue and/or cells.

The invention achieves the foregoing objects by directing at least two beams of laser irradiation at an affected area of body tissue, wherein the irradiation (a) is of low intensity at tissue impingement and (b) is also of spectral wavelength that is preferably in the visible red or in the infrared. Perturbations result in the affected cells either directly by reason of differences in the physical properties of the respective beams or indirectly by reason of interaction between the two beams at or near the situs of delivery to the affected body tissue.

DETAILED DESCRIPTION

The invention will be described in detail for presently preferred apparatus, in conjunction with the accompanying drawings, in which.

Figure 1:
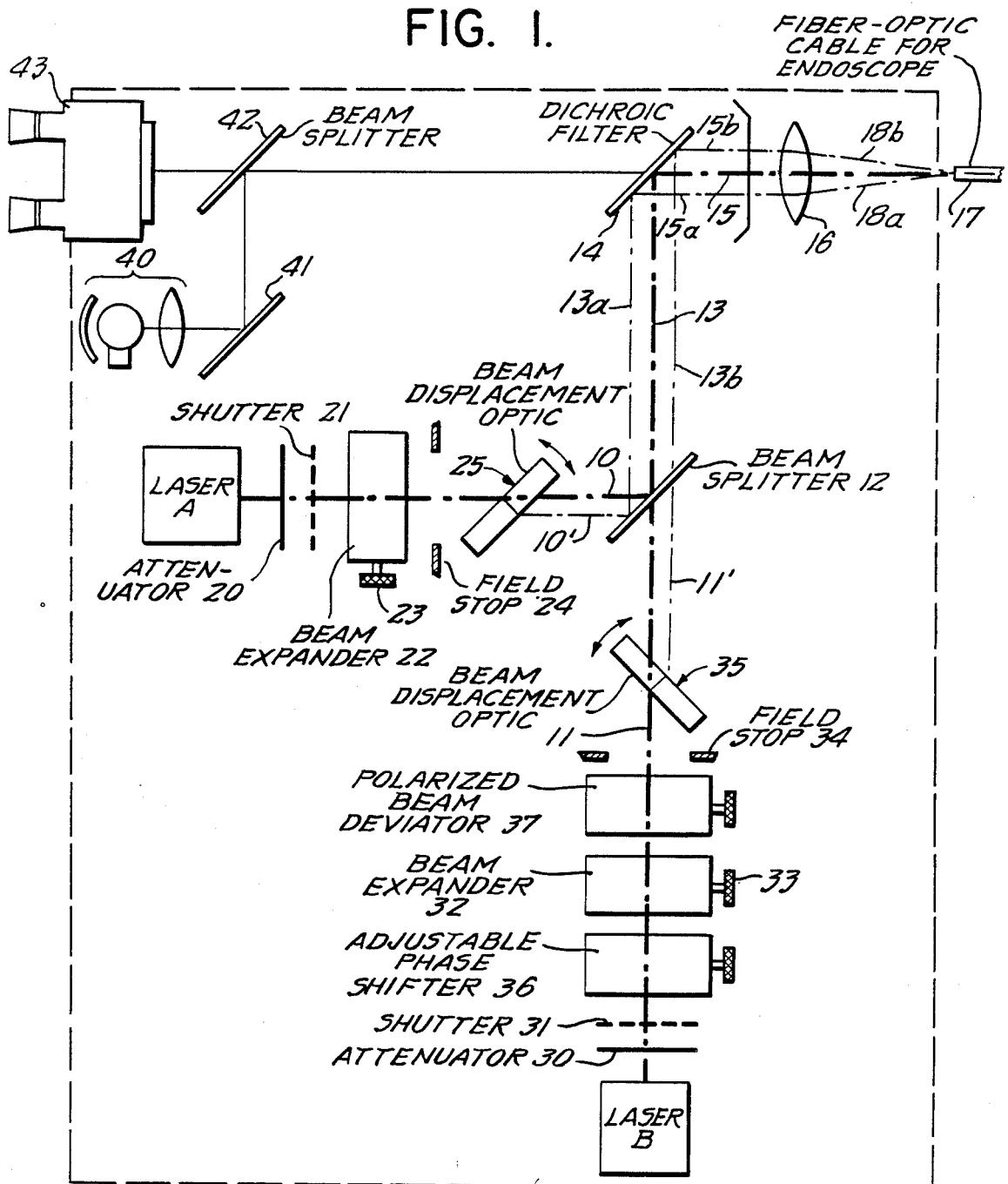
FIG. 1 is an optical diagram schematically indicating components of apparatus of the invention.

In FIG. 1, a first laser A delivers an output beam on a first optical axis 10, and a second laser B delivers an output beam on a second optical axis 11 which is orthogonally oriented for intersection and folded merger with axis 10 at a beam splitter 12. As a consequence, both laser beams utilize a common axis 13 of therapeutic energy delivery which, in the form shown, employs a dichroic filter 14 to fold projected laser energy onto a delivery axis 15. The delivered energy may be in the form of a collimated beam, producing a circular or otherwise configured spot at impact with living tissue to be irradiated; alternatively, as suggested by converging-lens means 16, the laser energy may be converged to a lesser area for coupling to a fiber-optic delivery system 17, as in the case of an endoscope utilization.

Each of the lasers A, B preferably emits in the visible red or in the infrared and at extremely low power, in terms of energy delivered to body tissue, thus avoiding local heating or coagulation of tissues and/or cells. Suitable and reasonably priced helium-neon, krypton and diode lasers are available for present purposes, and modes of use will determine particular selection.

To further facilitate particular desired modes of use, optical elements on axis 10 are shown to include attenuator means 20 (which may be selectively variable), shutter means 21 (which may be mechanical and electromagnetically actuated, or electro-optical and electronically actuated), a beam expander 22 (with manual means 23 for adjusting expansion), a field stop 24, and a beam-displacement optic 25 (having provision for its adjustable tilt with respect to axis 10, as suggested by double-headed arcuate symbolism). In similar fashion, optical elements on axis 11 are shown to include attenuator means 30, shutter means 31, a beam expander 32 (with adjustment means 33), a field stop 34, and an adjustable-tilt beam-displacement optic 35; in addition, the optical elements on axis 11 are seen to include adjustable phase-shifter means 36 to enable selective phase offset of the axis 11 beam with respect to the axis 10 beam (in the event that lasers A and B are identical), and means 37 for selective angular shifting of the polarization of one with respect to the other of beams 10-11. A suitable polarization-rotator product of Newport Corporation is identified by Catalog Number PR-550 for use in the visible spectrum, or by Catalog Number PR-950 for use in the near-infrared (700 to 1200 nm).

Figure 2:
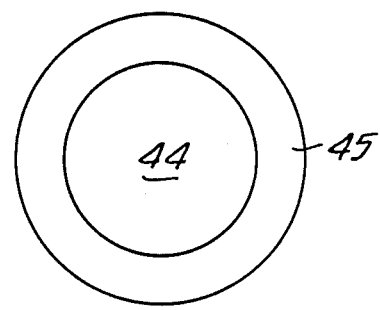
FIG. 2 is an enlarged diagram indicative of a beam-delivery embodiment.

To complete the description of components shown in FIG. 1, a field-illumination system 40 projects light onto the delivery axis 15, via a folding reflector 41 and a beam splitter 42, and a viewing device such as a stereo-observing biomicroscope 43 has a direct line of sight along axis 15. With both field stops 24, 34 adjusted to confine their respective beams to the same circular section, and with the two beam-displacement optics 25, 35 set for zero tilt (i.e., with their plane-parallel surfaces oriented normal to their respective optical axis 10, 11), the described system will deliver equal and coincident areas of radiation from both lasers A, B; if, on the other hand, one of stops 24, 34 is set for a larger beam-limiting section than the other, then delivered concentric overlap of radiation from the two lasers will be as depicted in FIG. 2, namely, with a central area 44 of concurrent response to both lasers, surrounded by a fringe annulus 45 of response to but one of the two lasers. The latter situation will be seen to have utility for a case wherein a buffer zone 45 of less-exposed tissue is desired between a central maximally treated zone and externally adjacent areas of untreated tissue.

As indicated generally above, it is the intention and purpose of the present invention to employ interaction between concurrent, or effectively concurrent, but dissimilar, laser beams of the character indicated to induce perturbations in affected tissue whereby vascular or like growth is enhanced beyond what may be achievable with emanations from a single laser. With the described apparatus, such dissimilarities are achieved through one or more of various combinations of beams on axes 10 and 11, as follows:

A. With identical lasers at A and B, as for example two He-Ne lasers, one on each of the axes 10, 11:

(1) Adjust phase shifter 36, so that combined output on delivery axis 15 is sum of two spatially and temporally coherent radiations at identical wavelength, but phase-displaced with respect to each other.

(2) Adjust polarization rotator 37, so that combined output on delivery axis 15 is the product of a predetermined difference in polarization-plane orientation for each of two spatially and temporally coherent radiations of identical wavelength.

(3) Adjust the beam-displacement optics 25, 35 for equal and opposite offsetting displacements of their respective axes (from 10 to 10', and from 11 to 11', respectively) so that the beam 13a (15a) for laser-A radiation may be converged on a first axis 18a to treated tissue, and so that the beam 13b (15b) for laser-B radiation may be converged on a second axis 18b to the same area of treated tissue.

(4) With a selected one of the modes (1), (2) or (3) above, operate the shutters (choppers) 21, 31 in synchronism, in accordance with a selected one of the following mode refinements:
  (a) shutter-open/shutter-closed, in coincident synchronism on both axes 10, 11.
  (b) shutter-open/shutter-closed, in time interlaced relation on the respective axes 10, 11.
  (c) shutter-open action on one axis (1) in only partial cyclical overlap with shutter-open action on the other axis (11).
  (d) cyclical rate of less than 15 Hz, to allow affected-cell recovery between shutter-open exposures.
  (e) cyclical rate greater than 15 Hz, to suppress affected-cell recovery during period of treatment.

B. With non-identical lasers at A and B, as for example, a He-Ne laser on axis 10 and a krypton laser on axis 11:

(5) Adjust attenuator 20 or 30 such that beam intensity at one wavelength on one axis (1) is equal to or greater than beam intensity at the other wavelength on the other axis (11).

(6) Adjust polarization rotator 37, so that the combined output on delivery axis 15 is the product of a predetermined difference in polarization-plane orientation for each of two spatially and temporally coherent radiations of different wavelengths.

(7) Adjust the beam-displacement optics 25, 35, for equal and opposite offsetting displacements of their respective axes (from 10 to 10', and from 11 to 11', respectively) so that the beam 13a (15a) for laser-A radiation may be converged on a first axis 18a to treated tissue, and so that the beam 13b (15b) for laser-B radiation may be converged on a second axis 18b to the same area of treated tissue.

(8) With a selected one of the modes (5), (6), or (7) above, operate the shutters (choppers) 21, 31 in synchronism in accordance with one of the mode refinements recited in mode A (4) above.

Whatever the selected variety of laser at A or B, it is recommended that the combined intensity of beam energy deliverable to the affected area of body tissue be in the order of microwatts/cm$^2$, as and preferably in the range of 100 to 150 microwatts/cm$^2$.

Figure 3:
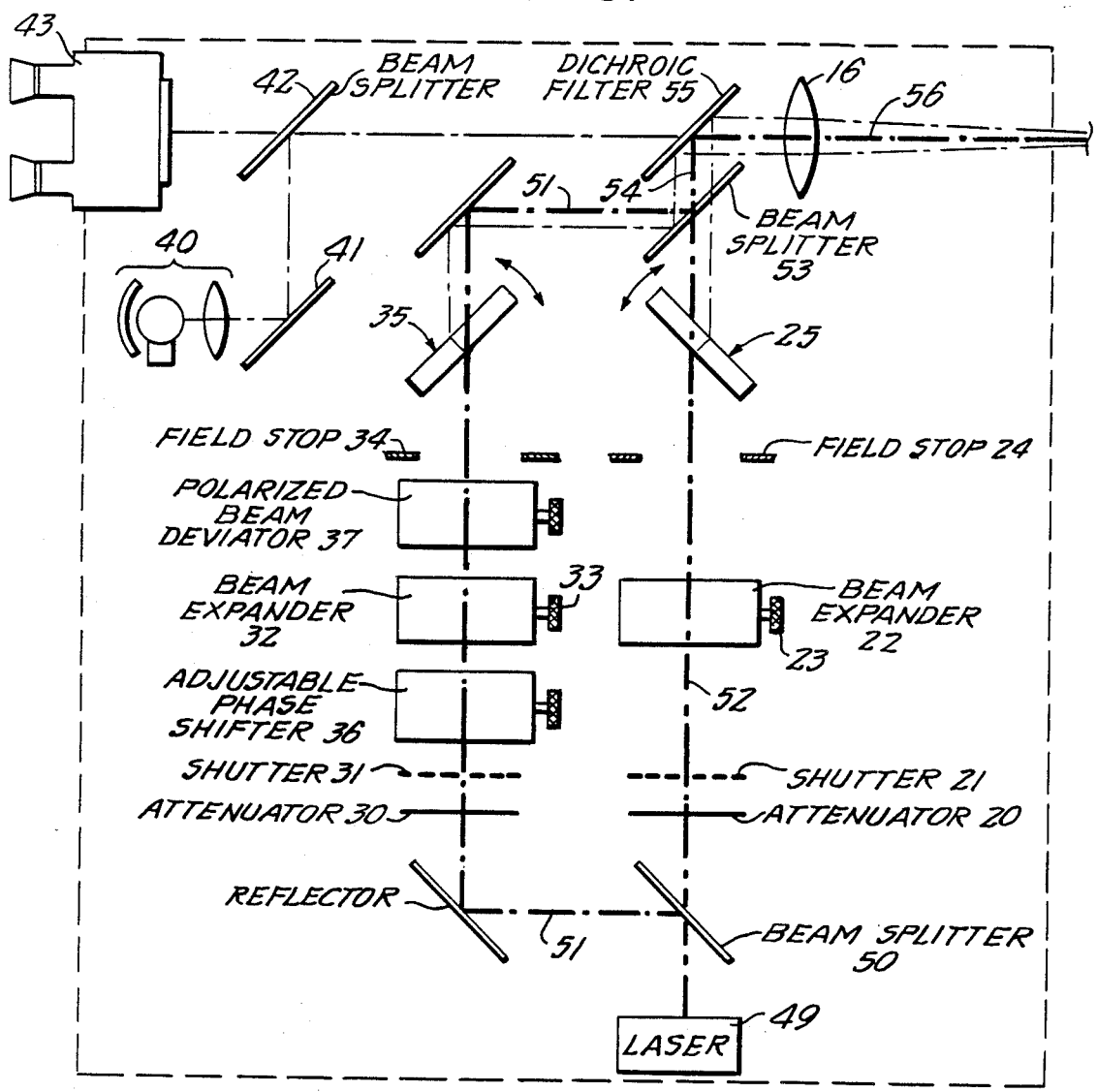
FIG. 3 is a diagram similar to FIG. 1 to show a modification.

In the embodiment of FIG. 3, the output beam from a single laser 49 is divided by a beam splitter 50 into beams 51, 52 on separate paths, which are thereafter recombined by beam-splitter means 53 to a single axis 54, before folding at a dichroic filter 55, to the delivery axis 56. Instrumentalities operative upon beam 52 are as described for the beam 10 from laser A in FIG. 1, and those operative upon beam 51 are as described for the beam 11 from laser B in FIG. 1; these instrumentalities, as well as illumination and viewing instrumentalities, have therefore been given the same reference numbers as in FIG. 1.

It will be seen that the single-laser embodiment of FIG. 3 is essentially the functional equivalent of the identical-laser situation mentioned above in connection with FIG. 1. The dissimilarities that may be produced in the divided beams 51, 52 of FIG. 3 may therefore include those tabulated under category A above for identical lasers on axes 10 and 11 of FIG. 1

Figure 4:
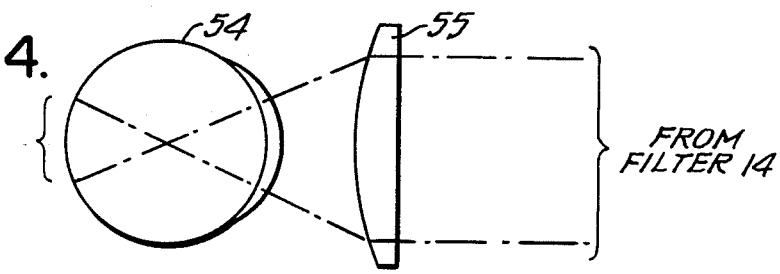
FIG. 4 is a simplified fragmentary optical diagram of one technique of laser-beam delivery within an eye, for either of the embodiments of FIG. 1 or FIG. 3.
Figure 5:
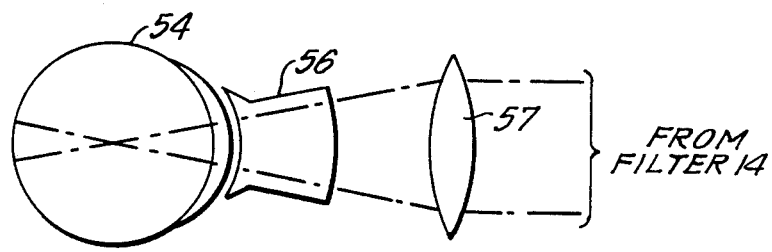
FIG. 5 is a diagram similar to FIG. 4 to show another technique of laser-beam delivery within an eye, for either of the embodiments of FIG. 1 or FIG. 3.

As to body-tissue application, the presently described multiple-beam exposures may be delivered either directly as a collimated beam wherein field-stop openings determine size and shape of a delivered spot or spots, or via a fiber-optic endoscope to an internal body-tissue region. For delivery within an eye 54, FIG. 4 illustrates use of a converging optic 55 to develop a relatively large area of exposure to the retina, while FIG. 5 illustrates use of a contact-lens element 56 in conjunction with a converging optic 57 to effect exposure over a more restricted area of the retina. It will be understood that beam cross-sectional areas delivered to the optic element 55 (or 56) will be determined by field-stop dimensional limitation, at legend-identified components of FIG. 1 or FIG. 3, as the case may be.

Parenthetic reference has been made above to choppers as having equivalence to shutters, for present purposes, with electrical or electronic control for their particular synchronized coordination; such controls are well understood and therefore need not now be described. It will also be understood that time-interlaced chopper action, as between two differently characterized laser beams delivered to body tissue, may be achieved by a rotary chopper having a flat mirror surface (1) that is inclined 45° to the one beam which is to be folded into axis alignment with that of the other beam, and (2) that the mirror surface is interrupted to provide an open sector space for non-reflected direct delivery of said other beam in interlace with reflected delivery of said one beam. In FIG. 1, such a mirror chopper is to be understood as symbolized by the 45°-inclined plane-parallel device called out as beam-splitter 12 in FIG. 1 or as beam-splitter 53 in FIG. 3.

It will further be understood that the operative limited spectral band of reflectivity at each of the dichroic filters 14 (55) will depend upon the particular selected lasers at A, B and 49. Thus, for HeNe and krypton lasers, the limited band of dichroic-filter reflectivity is suitably 610 to 660 nm, thereby allowing for field illumination (from 40) and viewing (from 43) via a generous remainder of the visible spectrum.

What is claimed is:

1. Apparatus for enhancement of vascular or other tissue growth by laser irradiation of a local area of living body tissue, comprising laser means producing first and second output beams of identical wavelength, means including a beam splitter for combining said beams for coordinated delivery to and interaction with tissue at said local area, and means operable upon one with respect to the other of said beams for determining a phase shift of one with respect to the other of said beams, the combined intensity of beam delivery to said area being in the range up to 150 microwatts/cm$^2$ and at least sufficient to therapeutically affect beam-impacted body tissue and/or cells but less than sufficient to induce photocoagulation, photovaporization, photonoptical-tissue breakdown, or photoablative decomposition of living tissue and/or cells.

2. Apparatus for enhancement of vascular or other tissue growth by laser irradiation of a local area of living body tissue, comprising laser means producing first and second output beams of identical wavelength, means including a beam splitter for combining said beams for coordinated delivery to and interaction with tissue at said local area, and means operable upon one with respect to the other of said beams for determining a polarization shift of one with respect to the other of said beams, the combined intensity of beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

3. Apparatus for enhancement of vascular or other tissue growth by laser irradiation of a local area of living body tissue, comprising laser means producing first and second output beams of identical wavelength, means including a beam splitter for combining said beams for coordinated delivery to and interaction with tissue at said local area, and means operable upon one with respect to the other of said beams for determining an intensity difference at one with respect to the other of said beams, the combined intensity of beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

4. Apparatus for enhancement of vascular or other tissue growth by laser irradiation of a local area of living body tissue, comprising laser means producing first and second output beams of identical wavelength, means including a beam splitter for combining said beams for coordinated delivery to and interaction with tissue at said local area, and means including a chopper operative upon at least one of said beams prior to incidence with said beam splitter, the combined intensity of beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

5. Apparatus for enhancement of vascular or other tissue growth by laser irradiation of a local area of living body tissue, comprising laser means producing first and second output beam of identical wavelength, means including a beam splitter for combining said beams for coordinated delivery to and interaction with tissue at said local area, and means including synchronized first and second choppers operative upon said respective beams prior to incidence with said beam splitter, the combined intensity of beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

6. Apparatus for enhancement of vascular or other tissue growth by laser irradiation of a local area of living body tissue, comprising a first laser producing a first output beam at a first wavelength, a second laser producing a second output beam at a second wavelength, and means including a rotatable chopper having a mirror surface for combining said beams for coordinated interlace of their delivery to and interaction with tissue at said area, the combined intensity of beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

7. Apparatus according to any one of claims 2, 3, 4, or 5 the intensity of beam energy deliverable to said area is in the range up to 150 microwatts/cm$^2$.

8. Apparatus according to any one of claims 2, 3, 4, 5 or 6 in which said wavelength is at least 600 nanometers.

9. Apparatus according to any one of claims 2, 3, 4 or 5, in which said laser means comprises a laser producing a single output, and means including a beam splitter exposed to said output for dividing the same into said first and second output beams.

10. Apparatus according to any one of claims 2, 3, 4, or 5, in which said laser means comprises a laser producing a single output, and means including a beam splitter exposed to said output for dividing the same into said first and second output beams, and in which said laser means is a helium-neon laser.

11. Apparatus according to any one of claims 2, 3, 4, or 5, in which said laser means comprises a laser producing a single output, and means including a beam splitter exposed to said output for dividing the same into said first and second output beams, and in which said laser means is a krypton laser.

12. Apparatus according to any one of claims 2, 3, 4, or 5, in which said laser means comprises a laser producing a single output, and means including a beam splitter exposed to said output for dividing the same into said first and second output beams, and in which said laser means is a diode laser.

13. Apparatus, according to any one of claims 2, 3, 4, 5, or 6, in which delivery of the energy of at least one of said beams is with spatial and temporal coherence.

14. Apparatus according to any one of claims 2, 3, 4, 5, or 6, in which delivery of the energy of each of said beams is with spatial and temporal coherence.

15. Apparatus according to any of claims 2, 3, 4, 5, or 6, in which delivery of the energy of the respective beams is on separate alignments which are convergent for substantial intersecting overlap at said local area.

16. Apparatus according to claim 2 or claim 3 in which said means operable upon one with respect to the other of said beams is selectively variable.

17. Apparatus according to claim 5 in which said choppers are electro-optical choppers.

18. Apparatus according to claim 5, in which said choppers are operative upon said beams in phase-interlaced relation.

19. Apparatus according to claim 5, in which said choppers are operative upon said beams in phase coincidence.

20. Apparatus according to claim 5, in which said choppers are operative upon said beams in phase-offset but at least partially overlapping relation.

21. Apparatus according to any one of claims 2, 3, 4, 5, or 6, in which the intensity of beam energy deliverable to said area is in the range of 100 to 150 microwatts/cm$^2$ and the wavelength of each of said beams is at least 600 nanometers, and in which, in addition to said beam splitter, said means for coordinated delivery includes a dichroic mirror which is of reflectance conforming substantially to beam-wavelength limitation, thereby establishing an axis of viewing said area through said dichroic mirror, and a viewing optical system on said axis.

22. Apparatus according to any one of claims 2, 3, 4, 5, or 6, in which the intensity of beam energy deliverable to said area is in the range of 100 to 150 microwatts/cm$^2$.

23. Apparatus according to claim 6, in which each of said wavelength is at least 600 nanometers.

24. Apparatus according to any one of claims 2, 3, 4, 5, or 6, in which the range of intensity of beam energy deliverable to said area includes the range 100 to 150 microwatts/cm$^2$.

25. Apparatus according to any one of claims 4, 5, or claim 6, in which the chopping rate exceeds substantially 15 per second.

26. Apparatus according to any one of claims 4, 5, or claim 6, in which the chopping rate is less than substantially 15 per second.

27. Apparatus for enhancement of vascular or other tissue growth by laser irradiation of a local area of living body tissue, comprising a first laser producing a first output beam at a first wavelength, a second laser producing a second output beam at a second wavelength, and means including a beam splitter for combining said beams for coordinate delivery to and interaction with tissue at said local area, the combined intensity of beam delivery to said area being in the range up to 150 microwatts/cm$^2$ and at least sufficient to therapeutically affect beam-impacted body tissue and/or cells but less than sufficient to induce photocoagulation, photovaporization, photonoptical-tissue breakdown, or photoablative decomposition of living tissue and/or cells.

28. Apparatus according to claim 27, in which at least one of said lasers is a diode laser.

29. Apparatus according to claim 27, in which each of said wavelengths is at least 600 nanometers.

30. Apparatus for enhancing or promoting vascular or other tissue growth in a living body, said apparatus comprising laser means for generating two low-power beams of laser radiation, and laser beam delivery means for delivering two low-power beams of laser radiation to a single local area of impact and interaction with body tissue, said beams differing physically in at least one respect and having a combined intensity which is in the range up to 150 microwatts/cm$^2$ and at least sufficient to therapeutically affect beam-impacted body tissue and/or cells and which is less than sufficient to induce photocoagulation, photovaporization, photonoptical-tissue breakdown, or photoablative decomposition of living tissue and/or cells.

31. Apparatus according to claim 30, in which said beams are of different wavelength.

32. Apparatus for enhancement of vascular or other tissue growth by laser irradiation of a local area of living body tissue, comprising laser means producing first and second output beams of identical wavelength, said laser means comprising a laser producing a single output, and means including beam-splitter means exposed to said output for dividing the same into said first and second output beams; means including a beam splitter for combining said beams for coordinated delivery to and interaction with tissue at said local area; and means operable upon one with respect to the other of said beams for determining a phase shift of one with respect to the other of said beams, the combined intensity of beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

33. Apparatus for enhancement of vascular or other tissue growth by laser irradiation of a local area of living body tissue, comprising helium-neon laser means producing first and second output beams of identical wavelength, means including a beam splitter for combining said beams for coordinated delivery to and interaction with tissue at said local area, and means operable upon one with respect to the other of said beams for determining a phase shift of one with respect to the other of said beams, the combined intensity of said beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

34. Apparatus for enchancement of vascular or other tissue growth by laser irradiation of a local area of living body tissue, comprising krypton laser means producing first and second output beams of identical wavelength, means including beam-splitter means for combining said beams for coordinated delivery to and interaction with tissue at said local area, and means operable upon one with respect to the other of said beams for determining a phase shift of one with respect to the other of said beams, the combined intensity of said beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

35. Apparatus for enhancement of vascular or other tissue growth by laser irradiation of a local area of living body tissue, comprising a helium-neon laser producing a first output beam at a first wavelength, a krypton laser producing a second output beam at a second wavelength, and means including a beam splitter for combining said beams for coordinated delivery to and interaction with tissue at said local area, the combined intensity of beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

36. Apparatus for enhancement of vascular or other tissue growth by laser irradiation of a local area of living body tissue, comprising laser means producing first and second output beams of identical wavelength, means including a beam splitter for combining said beams for coordinated delivery to and interaction with tissue at said local area, and means operable upon one with respect to the other of said beams for determining a phase shift of one with respect to the other of said beams, the delivery of the energy of the respective beams being on separate alignments which are convergent for substantial intersecting overlap at said local area, and the combined intensity of beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

37. Apparatus for enhancement of vascular or other tissue growth by laser irradiation of a local area of living body tissue, comprising a first laser producing a first output beam at a first wavelength, a second laser producing a second output beam at a second wavelength, and means including a beam splitter for combining said beams for coordinated delivery to and interaction with tissue at said local area, the delivery of the energy of the respective beams being on separate alignments which are convergent for substantial intersecting overlap at said local area, the combined intensity of beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

38. Apparatus for enhancing or promoting vascular or other tissue growth in a living body, said apparatus comprising laser means for delivering two low-power beams of laser radiation to a single local area of impact and interaction with body tissue, said beams being of the same wavelength and being directed to impact said area from different convergent aspects, and said beams having a combined intensity which is at least sufficient to therapeutically affect beam-impacted body tissue and/or cells and which is less than sufficient ti induce photocoagulation, photovaporization, photonoptical-tissue breakdown, or photoablative decomposition of living tissue and/or cells.

39. Apparatus for enhancing or promoting vascular or other tissue growth in a living body, said apparatus comprising laser means for delivering two low-power beams of laser radiation to a single local area of impact and interaction with body tissue, said beams being of the same wavelength but in phase-offset relation to each other, and said beams having a combined intensity which is at least sufficient to therapeutically affect beam-impacted body tissue photocoagulation, photovaporization, photonoptical-tissue breakdown, or photoablative decomposition of living tissue and/or cells.

40. Apparatus for enchancing or promoting vascular or other tissue growth in a living body, said apparatus comprising laser means for delivering two low-power beams of laser radiation to a single local area of impact and interaction with body tissue, said beams being polarized in mutually offset planes, and said beams having a combined intensity which is at least sufficient to therapeutically affect beam-impacted body tissue and/or cells and which is less than sufficient to induce photocoagulation, photovaporization photonoptical-tissue breakdown, or photoablative decomposition of living tissue and/or cells.

41. Apparatus for enhancing or promoting vascular or other tissue growth in a living body, said apparatus comprising laser means for delivering two low-power beams of laser radiation to a single local area of impact and interaction with body tissue, one of said beams being directed to impact body tissue over an area greater than but fully overlapping the area of impact by the other of said beams, said beams differing physically in at least one respect and having a combined intensity which is at least sufficient to therapeutically affect beam-impacted body tissue and/or cells and which is less than sufficient to induce photocoagulation, photovaporization, photonoptical-tissue breakdown, or photoablative decomposition of living tissue and/or cells.

42. Apparatus for enhancing or promoting vascular or other tissue growth in a living body, said apparatus comprising laser means for delivering two low-power beam of laser radiation to a single local area of impact and interaction with body tissue, said beams being of different wavelength and in chopped interlace, and said beams having a combined intensity which is at least sufficient to therapeutically affect beam-impacted body tissue and/or cells and which is less than sufficient to induce photocoagulation, photovaporization, photonoptical-tissue breakdown, or photoablative decomposition of living tissue and/or cells.

43. Apparatus for enhancement of vascular or other tissue growth by laser irradiation of a local area of living body tissue, comprising laser means producing first and second output beams of identical wavelength, means including a beam splitter for combining said beams for coordinated delivery to an interaction with tissue at said local area, and selectively variable means operable upon one with respect to the other of said beams for determining a phase of one with respect to the other of said beams, the combined intensity of beam delivery to said area being at least sufficient to therapeutically affect beam-impacted body tissue and/or cells but less than sufficient to induce photocoagulation, photovaporization, photonoptical-tissue breakdown, or photoablative decomposition of living tissue and/or cells.

44. The method of enhancing or promoting vascular or other tissue growth in a living body, which method comprises delivering two low-power beams of laser radiation to a single local area of impact and interaction with body tissue, said beams differing physically in at least one respect, and adjusting said beams for a combined intensity which is (a) in the range up to 150 microwatts/cm$^2$, (b) at least sufficient to therapeutically affect beam-impacted tissue and/or cells and (c) less than sufficient to induce photocoagulation, photovaporization, photonoptical-tissue breakdown, or photoablative decomposition of living tissue and/or cells.

* * * * *